United States Patent [19]

Butera et al.

[11] Patent Number: 5,403,854
[45] Date of Patent: Apr. 4, 1995

[54] SUBSTITUTED N-HETEROARYL-1,2-DIAMINOCYCLOBUTENE-3,4-DIONES

[75] Inventors: John A. Butera, Clarksburg; Schuyler A. Antane, Plainsboro, both of N.J.

[73] Assignee: American Home Products Corporation, Madison, N.J.

[21] Appl. No.: 259,212

[22] Filed: Jun. 13, 1994

Related U.S. Application Data

[62] Division of Ser. No. 153,706, Nov. 17, 1993, Pat. No. 5,354,763.

[51] Int. Cl.⁶ .................. C07D 231/56; A61K 31/415
[52] U.S. Cl. ..................................... 514/415; 514/395; 548/304.4; 548/362.5
[58] Field of Search .................. 548/362.5; 514/405, 514/415, 395

[56] References Cited

U.S. PATENT DOCUMENTS 4,390,701 6/1983 Algieri et al. .................. 546/235
4,673,747 6/1987 Nohara et al. .................. 546/334

FOREIGN PATENT DOCUMENTS 0426379 5/1991 European Pat. Off. .

OTHER PUBLICATIONS

Tietze, et al., Squaric Acid Diethyl Ester: A New Coupling Reagent for the Formation of Drug Biopolymer Conjugates. Synthesis of Squaric Acid Ester Amides and Diamides, Chem. Ber., 124, p. 1215, 1991.

Tietze, et al., Conjugation of p-Aminophenyl Glycosides with Squaric Acid Diester to a Carrier Protein and the Use of Neoglycoprotein in the histochemical Detection of Lectins, Bioconjugate Chem., 2, p. 148, 1991.

Ehrhardt, et al., Amide und Thioamide der Quadratsaure: Synthese und Reaktionen, Chem. Ber., 110, p. 2506, 1977.

Neuse, et al., Amidierung von Quadratsaure-estern, Liebigs Ann. Chem., p. 619, 1973.

Primary Examiner—C. Warren Ivy
Assistant Examiner—Zinna N. Davis
Attorney, Agent, or Firm—Richard K. Jackson

[57] ABSTRACT

The compounds of the formula:

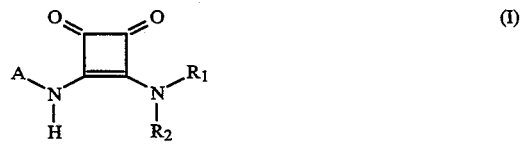

(I)

wherein:

$R_1$ and $R_2$ are, independently, hydrogen, straight or branched chain alkyl or mono- or bi-cyclic alkyl;

A is a benzodiazole of the formula:

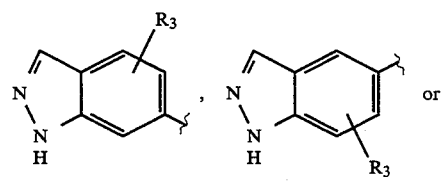

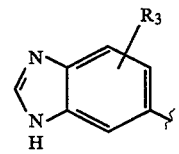

wherein:

$R_3$ is hydrogen, alkyl, perfluoroalkyl, alkoxy, perfluoroalkoxy, amino, alkylamino, dialkylamino, alkylsulfonamido, alkylcarboxamido, nitro, cyano or carboxyl;

or a pharmaceutically acceptable salt thereof, are smooth muscle relaxants.

6 Claims, No Drawings

SUBSTITUTED N-HETEROARYL -1,2-DIAMINOCYCLOBUTENE-3,4-DIONES

This is a division of application Ser. No. 08/153,706, filed Nov. 17, 1993, now U.S. Pat. No. 5,354,763.

BACKGROUND OF THE INVENTION

The present invention relates to novel 1,2-diamino derivatives of cyclobutene 3-4-diones having pharmacological activity, to a process for their preparation, to pharmaceutical compositions containing them, and to their use in the treatment of disorders associated with smooth muscle contraction; via potassium channel modulation. Such disorders include, but are not limited to: urinary incontinence, hypertension, asthma, premature labor, irritable bowel syndrome, congestive heart failure, angina, and cerebral vascular disease.

Stemp et at. disclose a class of amino substituted cyclobutenedione derivatives of chromans described as having blood pressure lowering activity and bronchodilatory activity in EP-426379-A2. Several series of 1-amino-2-phenylalkylamino-cyclobutene-3,4-diones are reported as H-2 receptor antagonists by Algieri et at. in U.S. Pat. No. 4,390,701. Several related 1-amino-2-phenoxyalkylamino derivatives are disclosed by Nohara et at. in U.S. Pat. No. 4,673,747.

The syntheses of variously substituted 1,2-diaminocyclobutene-3,4-diones are described in the following publications: Tietze et at., *Chem Ber.* 1991, 124, 1215; Tietze et at., *Bioconjugate Chem.* 1991, 2, 148; Ehrhardt et al., *Chem. Ber.* 1977, 110, 2506, and Neuse et at., *Liebigs Ann. Chem.* 1973, 619.

DESCRIPTION OF THE INVENTION

Accordingly, the present invention discloses compounds represented by the formula (I):

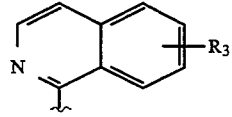

wherein:
R$_1$ and R$_2$ are, independent from each other, hydrogen, C$_{1-10}$ straight chain alkyl, C$_{1-10}$ branched alkyl, or C$_{3-10}$ cyclic or bicyclic alkyl;
A is selected from the group consisting of:

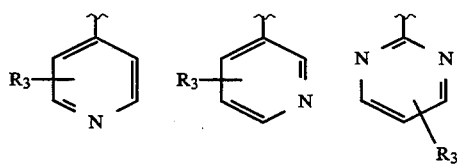

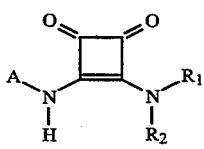

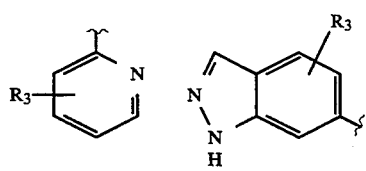

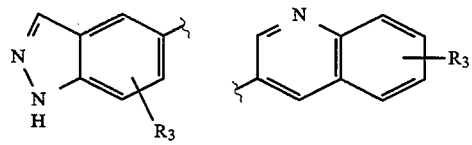

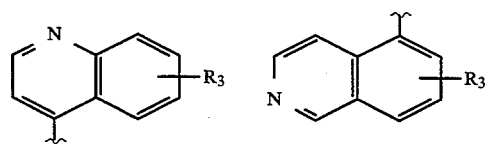

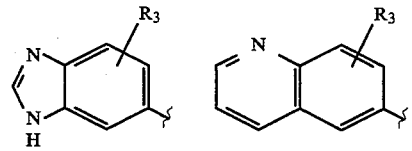

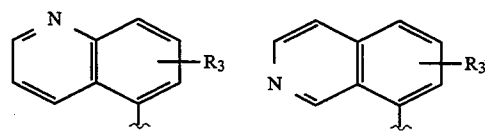

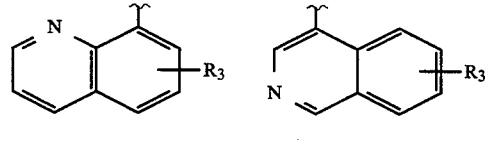

wherein:
R$_3$ is hydrogen, C$_{1-6}$ alkyl, C$_{1-6}$ perfluoroalkyl, C$_{1-6}$ alkoxy, C$_{1-6}$ perfluoroalkoxy, amino, C$_{1-6}$ alkylamino, C$_{2-12}$ dialkylamino, C$_{1-6}$ alkylsulfonamido, alkyl-carboxamido containing 2 to 7 carbon atoms, nitro, cyano, carboxyl;

or, A is a substituted phenyl group of the following formula:

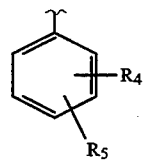

wherein:
R$_4$ and R$_5$, independent from each other, are selected from the following: cyano, nitro, amino, C$_{1-6}$ alkyl, C$_{1-6}$ perfluoroalkyl, C$_{1-6}$ alkoxy, C$_{1-6}$ perfluoroalkoxy, amino, C$_{1-6}$ alkylamino, C$_{2-12}$ dialkylamino, sulfamyl, C$_{1-6}$ alkylsulfonamido, C$_{6-12}$ arylsulfonamido, alkylcarboxamido containing 2 to 7 carbon atoms, arylcarboxamido containing 7 to 13 carbon atoms, C$_{1-6}$ alkylsulfone, C$_{1-6}$ perfluoroalkylsulfone, C$_{6-12}$ arylsulfone, chloro, bromo, fluoro, iodo, 1-imidazolyl, carboxyl or hydrogen, with the proviso that R$_4$ and R$_5$ cannot be hydrogen simultaneously;

or a pharmaceutically acceptable salt thereof.

A preferred aspect of this invention includes compounds of formula (I) wherein:
$R_1$ and $R_2$ are as stated above;
A is selected from the following:

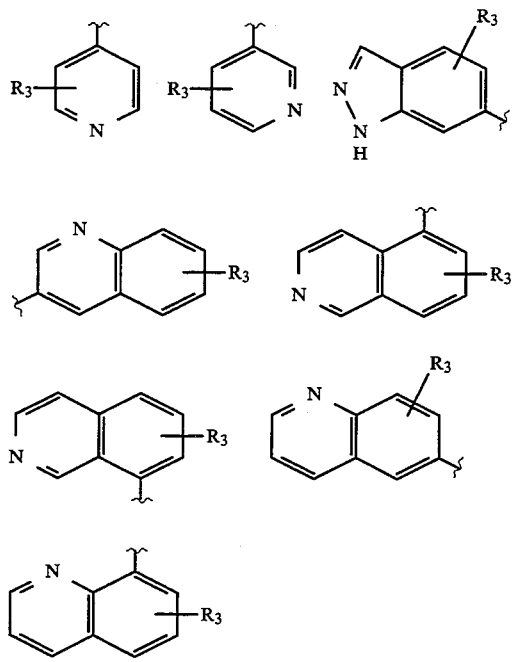

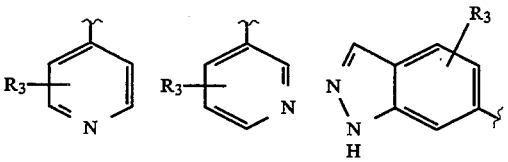

wherein:
$R_3$ is as stated above;
or, A is a substituted phenyl group of the following formula:

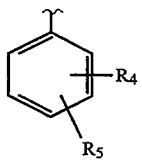

wherein:
$R_4$ and $R_5$, independent from each other, are selected from the following: cyano, nitro, amino, chloro, bromo, fluoro, iodo, 1-imidazolyl, carboxyl or hydrogen, with the proviso that $R_4$ and $R_5$ cannot be hydrogen simultaneously;
or a pharmaceutically acceptable salt thereof.

The most preferred aspect of this invention includes compounds of formula (I) wherein:
$R_1$ and $R_2$ are as stated above;
A is selected from the following:

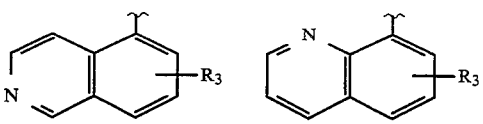

wherein:
$R_3$ is as stated above;
or, A is a substituted phenyl group of the following formula:

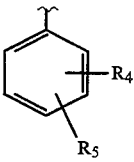

wherein:
$R_4$ and $R_5$, independent from each other, are selected from the following: cyano, nitro, amino, chloro, bromo, fluoro, iodo, 1-imidazolyl, carboxyl or hydrogen, with the proviso that $R_4$ and $R_5$ cannot both be hydrogen simultaneously;
or a pharmaceutically acceptable salt thereof.

It is understood that the definition of the compounds of formula (I), when $R_1$, $R_2$, $R_3$, $R_4$. or $R_5$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where R3, R4, or R5 is a carboxyl group, salts of the compounds of this invention may be formed with bases such as alkali metals (Na, K, Li) or the alkaline earth metals (Ca or Mg).

The present invention also provides a process for the preparation of a compound of formula (I). More particularly, the compounds of formula (I) may be prepared by reacting a compound of formula (II):

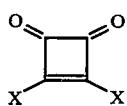 (II)

wherein X is a suitably designed leaving group such as methoxy, ethoxy, isopropoxy, halogeno, or a similar leaving group, with a compound of formula (III):

$A_1$—$NH_2$ (III)

wherein $A_1$ is A, as defined hereinbefore or a group of atoms convertible thereto, followed by treatment with a compound of formula (IV):

 (IV)

wherein $R_{a1}$ and $R_{a2}$ are $R_1$ and $R_2$, respectively, as defined hereinbefore or a group of atoms convertible thereto in a solvent such as ethanol or methanol at elevated temperatures.

As mentioned previously, the compounds of formula (I) have been found to relax smooth muscle. They are therefore useful in the treatment of disorders associated with smooth muscle contraction, disorders involving excessive smooth muscle contraction of the urinary tract (such as incontinence), or of the gastrointestinal tract (such as irritable bowel syndrome), asthma, and hair loss. Furthermore, the compounds of formula (I) are active as potassium channel activators which render them useful for treatment of peripheral vascular disease, hypertension, congestive heart failure, stroke, anxiety, cerebral anoxia and other neurodegenerative disorders.

The present invention accordingly provides a pharmaceutical composition which comprises a compound of this invention and a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

3-(Pyridin-4-ylamino)-4-(1,2,2-trimethyl-propylamino)-cyclobut-3-ene-1,2-dione

Step 1

Preparation of 3-(pyridin-4-ylamino)-4-ethoxy-cyclobut-3-ene-1,2-dione

To a solution of 3,4-diethoxy-3-cyclobutene-1,2-dione (5.00 g, 29.4 mmol) in absolute ethanol (100 mL) was added a suspension of 4-aminopyridine (2.77 g, 29.4 mmol) in ethanol (50 mL). The reaction mixture was refluxed for 4 hours then concentrated to give crude product. Chromatography (EtOAc) afforded 0.632 g (10%) of a white solid: mp 120°–125° C.

Step 2

Preparation of 3-(pyridin-4-ylamino)-4-(1,2,2-trimethyl-propylamino)-cyclobut-3-ene-1,2-dione To the above squarate (0.332 g, 1.52 mmol) in acetonitrile (30 mL) was added 2-amino-3,3-dimethylbutane (0.200 ml, 1.52 mmol). A precipitate formed while stirring overnight. The crude reaction mixture was vacuum filtered and the precipitate was dried in vacuo to yield 0.328 g (79%) of a pale yellow solid: mp 255°–257° C.; $^1$H NMR (DMSO-d$_6$): δ9.80 (s, 1H), 8.42 (dd, 2H), 7.72 (d, 1H), 7.45 (dd, 2H), 3.96–4.00 (m, 1H), 1.18 (s, 3H), 0.91 (s, 9H). IR (KBr): 3200, 1800, 1675, 1600 cm$^{-1}$; MS (m/z) 274 (MH+).

Elemental analysis for $C_{15}H_{19}N_3O_2$ Calc'd: C, 65.91; H, 7.01; N, 15.37; Found: C, 65.91; H, 6.96; N, 15.22.

EXAMPLE 2

(Exo)-3-(bicyclo[2,2,1]hept-2-ylamino)-4-(pyridin-4-ylamino)-cyclobut-3-ene-1,2-dione To the product of Example 1, Step 1 (0.332 g, 1.52 mmol) in acetonitrile (30 mL) was added (±) exo-2-aminonorbornane (0.180 mL, 1.52 mmol). A precipitate forms while stirring overnight. The reaction mixture was vacuum filtered and the precipitate was dried in vacuo to yield 0.350 g (81%) of a pale yellow solid: mp 268–270° C. (dec); $^1$H NMR (DMSO-d$_6$): δ9.70 (s, 1H), 8.40 (d, 2H), 7.74 (d, 1H), 7.42 (d, 2H), 3.90–3.95 (m, 1H), 2.23–2.31 (m, 2H), 1.78–1.84 (m, 1H), 1.09–1.54 (m, 7H). IR (KBr): 3200, 1795, 1670, 1600 cm$^{-1}$; MS (m/z) 283 (M+).

Elemental analysis for $C_{16}H_{17}N_3O_2$ Calc'd: C, 67.83; H, 6.05; N, 14.83; Found: C, 67.48; H, 6.03; N, 14.66.

EXAMPLE 3

3-(Pyridin-3-ylamino)-4-(1,2,2-trimethyl-propylamino)-cyclobut-3-ene-1,2-dione

Step 1

Preparation of 3-(pyridin-3-ylamino)-4-ethoxy-cyclobut-3-ene-1,2-dione

To a solution of 3,4-diethoxy-3-cyclobutene-1,2-dione (5.00 g, 29.4 mmol) in absolute ethanol (100 mL) was added a suspension of 3-aminopyridine (2.77 g, 29.4 mmol) in ethanol (50 mL). The mixture was heated at reflux for 18 hours, then concentrated. Chromatography (4:1 EtOAc/hexane) afforded 3.15 g (49%)of a white solid: mp 140°–145° C.

Step 2

Preparation of 3-(pyridin-3-ylamino)-4-( 1,2,2-trimethyl-propylamino )-cyclobut- 3-ene- 1,2-dione To the above squarate (0.328 g, 1.50 mmol) in acetonitrile (30 mL) was added 2-amino-3,3-dimethylbutane (0.200 mL, 1.52 mmol). A precipitate forms while stirring overnight. The crude reaction mixture was vacuum filtered and the precipitate was dried in vacuo to yield 0.27 g (66%) of a white solid: mp 243°–245° C.; $^1$H NMR (DMSO-d$_6$): δ9.67 (s, 1H), 8.58 (d, 1H),7.98 (d, 1H), 7.66 (d, 1H), 7.38 (m, 1H), 3.96–4.00 (m, 1H), 1.18 (s, 3H), 0.95 (s, 9H); IR (KBr): 3200, 1800, 1665, 1600 cm$^{-1}$. MS (m/z) 273 (M+).

Elemental analysis for C$_{15}$H$_{19}$N$_3$O$_2$ Calc'd: C, 65.91; H, 7.01; N, 15.37; Found: C, 65.92; H, 6.95; N, 15.24.

EXAMPLE 4

3-(2-Methylethylamino)-4-(pyridin-3-ylamino)(cyclobut3-ene-1,2-dione

To the product from Example 3, Step 1 (0.180 g, 0.825 mmol) in acetonitrile (100 mL) was added isopropylamine (20 mL, 235 mmol). The reaction was stirred at room temperature overnight, then concentrated. Trituration with ethylacetate/diethylether afforded 0.135 g (71%) of a white solid: mp 258°–260° C.; $^1$H NMR (DMSO-d$_6$): δ9.62 (br s, 1H), 8.55 (s, 1H), 8.22 (d, 1H), 7.94 (br d, 1H), 7.73 (br s, 1H), 7.36 (dd, 1H), 4.20 (br m, 1H), 1.25 (d, 6H). IR (KBr): 3200, 1800, 1660, 1610 cm$^{-1}$; MS (m/z) 231(M+).

Elemental analysis for C$_{12}$H$_{13}$N$_3$O$_2$ Calc'd: C, 62.32; H, 5.66; N, 18.17; Found: C, 62.86; H, 5.79; N, 18.53.

EXAMPLE 5

3-Dimethylamino-4-(pyridin-3-ylamino)-cyclobut-3-ene-1,2-dione

To the product from Example 3, Step 1 (0.330 g, 1.51 mmol) in acetonitrile (200 mL) was introduced to a stream of dimethylamine gas (15 minutes). The resultant solution was stirred overnight at room temperature, concentrated, and triturated with dichloromethane/diethylether to afford 0.278 g (85%) of an white solid: mp 235°–237° C.; $^1$H NMR (DMSO-d$_6$): δ9.50 (s, 1H), 8.46 (s, 1H), 8.22 (d, 1H), 7.60 (d, 1H), 7.32 (dd, 1H). IR (KBr): 1790, 1685, 1600 cm$^{-1}$; MS (m/z) 217 (M+).

Elemental analysis for C$_{11}$H$_{11}$N$_3$O$_2$ Calc'd: C, 60.82; H, 5.10; N, 19.34; Found: C, 60.71; H, 5.07; N, 19.46.

EXAMPLE 6

3-Amino-4-(pyridin-3-ylamino)-cyclobut-3-ene-1,2-dione

To the product from Example 3, Step 1 (0.330 g, 1.51 mmol) in acetonitrile (200 mL) was introduced to a stream of ammonia gas until solution became turbid. The resultant mixture was stirred overnight at room temperature. The precipitate was vacuum filtered and dried to afford 0.266 g (93%) of a white solid: mp 297° C.(dec); $^1$H NMR (DMSO-d$_6$): δ8.56 (s, 1H), 8.22 (d, 1H), 7.92 (d, 1H), 7.37 (m, 1H). IR (KBr): 3200, 1800, 1670, 1625 cm$^{-1}$; MS (m/z) 189 (M+).

Elemental analysis for C$_9$H$_7$N$_3$O$_2$ Calc'd: C, 57.14; H, 3.73; N, 22.21; Found: C, 57.18; H, 3.69; N, 22.10.

EXAMPLE 7

3-Tert-butylamino-4-(pyridin-3-ylamino)-cyclobut-3-ene-1,2-dione

The product from Example 3, Step 1 (2.60 g, 11.9 mmol) was dissolved in tert-butylamine (50 mL). The solution was refluxed for three hours, cooled, and concentrated in vacuo. Trituration with diethylether afforded 1.05 g (36%) of a white solid: mp 250°–252° C.; $^1$H NMR (DMSO-d$_6$): δ8.57 (s, 1H), 8.23 (d, 1H), 7.96 (d, 1H), 7.37 (m, 1H) 1.43 (s,9H). IR (KBr): 1790, 1685, 1600 cm$^{-1}$; MS (m/z) 245 (M+).

Elemental analysis for C$_{13}$H$_{15}$N$_3$O$_2$ Calc'd: .C, 63.66; H, 6.16; N, 17.13; Found: C, 63.28; H, 6.22; N, 17.07.

EXAMPLE 8

3-Tert-butylamino-4-(isoquinolin-5-ylamino)-cyclobut-3-ene-1,2-dione

Step 1

Preparation of 3-(isoquinolin-5-ylamino)-4-ethoxy-cyclobut-3-ene-1,2-dione

To a solution of 3,4-diethoxy-3-cyclobutene-1,2-dione (5.00 g, 29.4 mmol) in absolute ethanol (100 mL) was added a suspension of 5-aminoisoquinoline (4.24 g, 29.4 mmol) in ethanol (50 mL). The mixture was heated to reflux overnight and then filtered to yield 2.30 g (29%) of solid: mp 182(dec) ° C.

Step 2

Preparation of 3-Tert-butylamino-4-(isoquinolin-5-ylamino)-cyclobut-3-ene- 1,2-dione one-eighth Hydrate The above squarate (0.300 g, 1.12 mmol) was dissolved in tert-butylamine (50 mL) and refluxed for three hours. The mixture was cooled, concentrated, and triturated with diethylether to afford 0.120 g (39%) of the title compound as a white solid, one-eighth hydrate: mp 268°–270° C.(dec); $^1$H NMR (DMSO-d$_6$): δ9.75 (s, 1H), 9.35 (s, 1H), 8.62 (d, 1H), 8.19 (s, 1H), 8.01 (d, 1H), 7.88 (d, 1H), 7.68 (t, 1H), 1.47 (s, 9H). IR (KBr): 3200, 1785, 1670, 1600 cm$^{-1}$; MS (m/z) 295 (M+).

Elemental analysis for C$_{17}$H$_{17}$N$_3$O$_2$. 0.125 (H$_2$O) Calc'd: .C, 68.61; H, 5.84; N, 14.12; Found: C, 68.08; H, 5.78; N, 13.75.

EXAMPLE 9

3-Amino-4-(isoquinolin-5-ylamino)-cyclobut-3-ene-1,2-dione

A suspension of the the product from Example 8, Step 1 (0.190 g, 0.700 mmol) in ethanol (3.5 mL) was saturated with ammonia, capped, and heated to 45° C. for three hours. The mixture was cooled, concentrated, and triturated with diethylether. Crude product was recrystallized from dimethylformamide/water to give 0.129 g (77%) of the title compound as a pale yellow solid, one-eighth hydrate: mp 215° C.; $^1$H NMR (DMSO-d$_6$): δ9.87 (s, 1H), 9.34 (s, 1H), 8.60 (d, 1H), 7.40–8.60 (broad signal, NH2), 8.02 (d, 1H), 7.86 (d, 1H), 7.77 (d, 1H), 7.68 (t, 1H). IR (KBr): 3200, 1800, 1690, 1650 cm$^{-1}$; MS (m/z) 240(MH+).

Elemental analysis for C$_{13}$H$_9$N$_3$O$_2$.0.125 (H$_2$O) Calc'd: C, 64.66; H, 3.86; N, 17.40; Found: C, 64.10; H, 3.74; N, 16.99.

EXAMPLE 10

3-(Quinolin-8-ylamino)-4-(1,2,2-trimethyl-propylamino)-cyclobut-3-ene-1,2-dione

Step 1

Preparation of 3-(quinolin-8-ylamino)-4-ethoxy-cyclobut-3-ene-1,2-dione

To a solution of 8-aminoquinoline (1.00 g, 6.94 mmol) in ethanol (20 mL) was added 3,4-diethoxy-3-cyclobutene-1,2-dione (1.03 mL, 6.94 mmol) and the resulting mixture was heated to reflux for 24 hours. The mixture was cooled, diluted with ethanol, and filtered. The crude product was triturated with chloroform/hexanes, then purified by chromatography (EtOAc/hexane) to give 1.31 g (70%) of product: $^1$H NMR (DMSO-d$_6$) δ9.75 (br m, 1H), 8.86 (dd, 1H), 8.26 (br m, 1H), 8.20 (dd, 1H), 7.57 (m, 2H), 7.53 (dd, 1H), 4.95 (q, 2H), 1.59 (t, 3H).

Step 2

Preparation of 3-(quinolin-8-ylamino)-4-(1,2,2-trimethylpropylamino)-cyclobut-3-ene-1,2-dione To the above squarate (0.300 g, 1.12 mmol) in ethanol (5 mL) was added 2-amino-3,3-dimethylbutane (0.18 mL, 1.34 mmol) and the resulting mixture was heated at 45° C. overnight, diluted with hexanes, and filtered to give 0.294 g (81%) of a yellow solid: mp 244–245; $^1$H NMR (DMSO-d$_6$) δ10.45 (s, 1H), 8.97 (dd, 1H), 8.62 (d, 1H), 8.41 (dd, 1H), 8.29 (dd, 1H), 7.6 (m, 3H), 4.10 (m, 1H), 1.21 (d, 3H) 0.94(s, 9H). IR(KBr):3280, 2960, 1790, 1670cm$^{-1}$; MS (m/z) 323 (MH+).

Elemental analysis for C$_{19}$H$_{21}$N$_3$O$_2$ Calc'd: C, 70.56; H, 6.54; N, 12.99; Found: C, 70.38; H, 6.51; N, 12.94.

EXAMPLE 11

3-Methylamino-4-(quinolin-8-ylamino)-cyclobut-3-ene-1,2-dione

To the product from Example 10, Step 1 (0.64 g, 2.38 mmol) was added ethanolic methylamine (8.03M, 13 mL) and the mixture was stirred at 25° C. for 6 hours. Diethyl ether was added, and the resulting solid was filtered and washed with additional ether. Chromatography (EtOAc/hexanes) followed by trituration with dimethylsulfoxide/water afforded 0.398 g (66%) of product as a yellow solid: mp 236°–237° C.; $^1$H NMR (DMSO-d$_6$) δ10.32 (s, 1H), 8.95 (dd, 1H), 8.63 (m, 1H), 8.40 (dd, 1H), 8.26 (d, 1H), 7.68–7.54 (m, 3H), 3.27 (d, 3H). IR (KBr) 3200, 1795, 1610 cm$^{-1}$; MS (m/z) 253 (M+), 155 (100%).

Elemental analysis for C$_{14}$H$_{11}$N$_3$O$_2$ Calc'd: C, 66.39; H, 4.38; N, 16.59; Found: C, 66.13; H, 4.43; N, 16.48.

EXAMPLE 12

3-Amino-4-(quinolin-8-ylamino)-cyclobut-3-ene-1,2-dione

Ammonia gas was bubbled through a slurry of the product from Example 10, Step 1 (0.640 g, 2.38 mmol) in ethanol (13 mL) at −35° C. After 6 hours, the mixture was diluted with diethylether and filtered. Chromatography (EtOAc/hexanes) followed by trituration with dimethylsulfoxide/water afforded 0.342 g (60%) of product as a yellow solid, quarter hydrate: mp 263° C. (dec); $^1$H NMR (DMSO-d$_6$) δ10.35 (s, 1H), 8.95 (dd, 1H), 8.45 (br s, 2H), 8.40 (dd, 1H), 8.28 (dd, 1H), 7.66–7.55 (m, 3H). IR (KBr) 3260, 1800 cm$^{-1}$; MS (m/z) 239 (M+), 211, 183, 155, 129 (100%).

Elemental analysis for C$_{13}$H$_9$N$_3$O$_2$.0.25 (H$_2$O) Calc'd: C, 64.06; H, 3.72; N, 17.24; Found: C, 63.28; H, 3.85; N, 16.99.

EXAMPLE 13

3-(Quinolin-3-ylamino)-4-(1,2,2-trimethyl-propylamino)-cyclobut-3-ene-1,2-dione

Step 1

Preparation of 3-(Quinolin-3-ylamino)-4-ethoxy-cyclobut-3-ene-1,2-dione

To a solution of 3-aminoquinoline (2.12 g, 14.69 mmol) in ethanol (60 mL) was added 3,4-diethoxy-3-cyclobutene-1,2-dione (2.50 g, 14.69 mmol) and the resulting mixture was heated to reflux for 24 hours. The mixture was cooled, filtered, and the product was washed with diethylether and dried in vacuo to give 3.14 g (80%) of yellow solid which was used without purification: $^1$H NMR (DMSO-d$_6$) δ11.14 (s, 1H), 8.92 (dd, 1H), 8.20 (dd, 1H), 7.90 (m, 2H), 7.63 (m, 2H).

Step 2

Preparation of 3-(Quinolin-3-ylamino)-4-(1,2,2-trimethyl-propylamino)-cyclobut-3-ene-1,2-dione To the above squarate (0.30 g, 1.12 mmol) in ethanol (8 mL) was added 2-amino-3,3-dimethylbutane (0.18 mL, 1.34 mmol) and the resulting mixture was heated at 50° C. overnight. The precipitate was filtered, washed with diethylether, and dried in vacuo to afford 0.30 g (83%) of product as a light tan solid: mp 242°–246° C.; $^1$H NMR (DMSO-d6) δ9.93 (s, 1H), 8.90 (d, 1H), 8.38 (br s, 1H), 7.97 (d, 1H), 7.84 (dd, 1H), 7.75–7.55 (m, 2H), 4.00 (m, 1H), 1.20 (d, 3H), 0.94 (s, 9H). IR (KBr) 3160, 2960, 1795, 1650cm$^{-1}$; MS (m/z) 324 (MH+).

Elemental analysis for C$_{19}$H$_{21}$N$_3$O$_2$ Calc'd: C, 70.57; H, 6.55; N, 12.99; Found: C, 70.97; H, 6.41; N, 13.04.

EXAMPLE 14

3-Tert-butylamino-4-(quinolin-3-ylamino)-cyclobut-3-ene-1,2-dione

To the product from Example 13, Step 1 (0.30 g, 1.12 mmol) in ethanol (8 mL) was added tert-butylamine (0.35 mL, 3.36 mmol) and the resulting mixture was heated at 60° C. overnight. The mixture was concentrated, and the residue was dissolved in ethylacetate. Addition of hexanes induced precipitation of product which was filtered and triturated with diethylether/hexanes. Filtration and drying afforded 0.28 g (85%) of the title compound as a yellow solid, three -quarter hydrate: mp 257°–260° C.; $^1$H NMR (DMSO-d$_6$) d 10.00 (br d, 1H), 8.9 (d, 1H), 8.4 (m, 1H), 8.02 (d, 1H), 7.96 (br d, 1H), 7.86 (dd, 1H), 7.66–7.54 (m, 2H), 1.45 (s, 9H). IR (KBr) 3400, 3200, 2980, 1785, 1680cm$^{-1}$; MS (m/z) 296 (MH+).

Elemental analysis for C$_{17}$H$_{17}$N$_3$O$_2$.0.75 (H$_2$O) Calc'd: C, 66.11; H, 6.04; N, 13.61; Found: C, 66.08; H, 5.86; N, 13.36.

EXAMPLE 15

3-(Quinolin-3-ylamino )-4-(1,1-dimethyl-propylamino)-cyclobut-3-ene-1,2-dione

To the product from Example 13, Step 1 (0.30 g, 1.12 mmol) in ethanol (7 mL) was added tert-amylamine (0.39 mL, 3.35 mmol). After 48 hours of stirring at 45°

C., an additional aliquot of amine (0.39 mL) was added. After 3 hours, the mixture was concentrated and the residue was triturated with hexane/diethylether to give 0.328 g (95%) of product as an off white solid, three-quarter hydrate: mp 234°–236° C.; 1H NMR (DMSO-d6) δ10.04 (br s, 1H), 8.9 (d, 1H), 8.4 (d, 1H), 7.95 (d, 1H), 7.86, (m, 2H), 7.6 (m, 2H), 1.78 (q, 2H), 1.40 (s, 6H), 0.89 (t, 3H). IR (KBr) 3370, 3240, 2960, 1785, 1680cm$^{-1}$; MS (m/z) 309 (M+).

Elemental analysis for $C_{18}H_{19}N_3O_2.0.75$ ($H_2O$) Calc'd: C, 66.96; H, 6.40; N, 13.01; Found: C, 67.11; H, 6.26; N, 13.05.

EXAMPLE 16

3-(6-Methoxy-quinolin-8-ylamino)-4-(1,2,2-trimethylamino)-cyclobut-3-ene-1,2dione Step 1

Preparation of 3-(6-Methoxy-quinolin-8-ylamino)-4-ethoxy-cyclobut-3-ene-1,2-dione In a procedure identical to Example 10, Step 1, 8-amino-6-methoxyquinoline (2.00 g, 11.48 mmol) was reacted with 3,4-diethoxy-3-cyclobutene-1,2-dione (1.70 mL, 11.48 mmol) to give 0.99 g (29%) of product: 1H NMR (DMSO-d6) δ10.21 (s, 1H), 8.75 (dd, 1H), 8.29 (dd, 1H), 7.61 (m, 2H), 7.17 (d, 1H), 4.76 (q, 2H), 3.90 (s, 3H), 1.40 (t, 3H).

Step 2

Preparation of 3-(6-Methoxy-quinolin-8-ylamino)-4-(1,2,2-trimethylpropylamino)-cyclobut-3-ene-1,2-dione In a procedure identical to Example 10, Step 2, the above squarate (0.25 g, 0.839 mmol) and 2-amino-3,3-dimethylbutane (0.13 mL, 1.01 mmol) were reacted to give 0.21 g (71%) of title compound as an off-white solid: mp 243°–245° C.; 1H NMR (DMSO-d6) δ10.43 (br s, 1H), 8.78 (dd, 1H), 8.64 (d, 1H), 8.28 (dd, 1H), 8.13 (d, 1H), 7.56 (dd, 1H), 7.02 (d, 1H), 4.11 (m, 1H), 3.88 (s, 3H), 1.20 (d, 3H), 0.94 (s, 9H). IR (KBr) 3400, 3220, 2950, 1780 cm$^{-1}$; MS (m/z) 353 (M+).

Elemental analysis for $C_{20}H_{23}N_3O_3$ Calc'd: C, 67.96; H, 6.55; N, 11.88; Found: C, 67.72; H, 6.56; N, 11.74.

EXAMPLE 17

3-(6-Methoxy-quinolin-8-ylamino)-4-methylamino-cyclobut-3ene-1,2-dione

The product from Example 16, Step 1 (0.25 g, 0.839 mmol) was added to 8N ethanolic methylamine (7 mL). The resulting mixture was stirred for 4 hours and filtered. The solid was recrystallized from dimethylsulfoxide/water to give 0.12 g (50%) of product as a yellow solid: mp >275° C.; 1H NMR (DMSO-d6) δ10.29 (br s, 1H), 8.75 (dd, 1H), 8.68 (br q, 1H), 8.27 (dd, 1H), 8.10 (d, 1H), 7.55 (m, 1H), 7.00 (d, 1H), 3.88 (s, 3H), 3.26 (d, 3H). IR (KBr) 3240, 1795 cm$^{-1}$; MS (m/z) 283 (M+), 185 (100%).

Elemental analysis for $C_{15}H_{13}N_3O_3$ Calc'd: C, 63.59; H, 4.62; N, 14.83; Found: C, 63.30; H, 4.58; N, 14.70;

EXAMPLE 18

3-Tert-butylamino-4-(quinolin-6-ylamino)-cyclobut-3-ene-1,2-dione

To a solution of 3,4-diethoxy-3-cyclobutene-1,2-dione (5.00 g, 29.4 mmol) in absolute ethanol (100 mL) was added a suspension of 6-aminoquinoline (4.24 g, 29.4 mmol) in ethanol (50 mL). The mixture was heated at reflux for 18 hours, cooled, and vacuum filtered to afford 6.64 g (84%) of crude product (mp: 185–187, dec) which was used without further purification. An aliquot (3.00 g, 11.2 mmol) was dissolved in tert-butylamine (50 mL). The solution was refluxed for three hours, cooled, and concentrated. The residue was recrystallized twice from ethanol then triturated with diethylether to give 1.05 g (31%) of the title compound as a pale yellow solid, one-quarter hydrate: mp 234°–236° C.; 1H NMR (DMSO-d6): δ9.92 (s, 1H), 8.76 (d, 1H), 8.24 (d, 1H), 8.01 (d, 1H), 7.98 (s, 1H), 7.97 (d, 1H), 7.88 (d, 1H), 7.48 (m, 1H), 1.45 (s, 9H). IR (KBr): 1780, 1665, 1610 cm$^{-1}$; MS (m/z) 295 (M+).

Elemental analysis for $C_{17}H_{17}N_3O_2.0.25$ ($H_2O$) Calc'd: C, 68.10; H, 5.88; N, 14.01; Found: C, 67.63; H, 5.92; N, 13.96.

EXAMPLE 19

3-Tert-butylamino-4-(1H-indazol-6-ylamino)-cyclobut-3-ene-1,2-dione

To a solution of 3,4-diethoxy-3-cyclobutene-1,2-dione (4.51 g, 26.5 mmol) in absolute ethanol (100 mL) was added a suspension of 6-aminoindazole (3.53 g, 29.4 mmol) in ethanol (50 mL). The mixture was refluxed for 18 hours, cooled, and vacuum filtered to afford 3.60 g (53%) of crude product which was used without further purification. An aliquot (2.00 g, 7.77 mmol) was dissolved in tert-butylamine (50 mL) and the resulting mixture was refluxed for three hours, cooled, and concentrated. The crude product was recrystallized from ethanol/water to give 0.45 g (19%) of the title compound as a white solid, dihydrate: mp 183°–185° C.; 1H NMR (DMSO-d6): δ13.00 (s, 1H), 9.74 (s, 1H), 7.97 (s, 1H), 7.92 (s, 1H), 7.88 (s, 1H), 7.70 (d, 1H), 7.05 (d, 1H), 1.44 (s, 9H). IR (KBr): 3200, 1790, 1655, 1600 cm$^{-1}$; MS (m/z) 284 (M+).

Elemental analysis for $C_{15}H_{16}N_4O_2.2$ ($H_2O$) Calc'd: C, 56.24; H, 6.29; N, 17.49; Found: C, 56.06; H, 6.29; N, 17.43.

EXAMPLE 20

3-(Isoquinolin-5-ylamino)-4-methylamino-cyclobut-3-ene-1,2-dione

To a solution of 3,4-diethoxy-3-cyclobutene-1,2-dione (5.00 g, 29.4 mmol) in absolute ethanol (100 mL) was added a suspension of 5-aminoisoquixtoline (4.24 g, 29.4 mmol) in ethanol (50 mL). The mixture was heated at reflux for 18 hours, cooled, and vacuum filtered to afford 2.30 g (29%) of crude product (mp: 182, dec) which was used without further purification. To an aliquot (0.335 g, 1.25 mmol) of the squarate in ethanol (1.5 mL) was added 33% methylamine in ethanol (1.4 mL). The mixture was heated to 40° C. for 15 minutes, cooled, and concentrated. Trituration with diethylether afforded crude product which was crystallized from a minimal amount of methanol to give 0.149 g (47%) of an pale yellow solid: mp 245°–250° C. (dec); 1H NMR (DMSO-d6): δ9.79 (s, 1H), 9.33 (s, 1H), 8.60 (d, 1H), 7.99 (d, 1H), 7.86 (d, 1H), 7.76 (br d, 1H), 7.66 (t, 1H), 7.76 (br s, 1H). IR (KBr): 3200, 1800, 1680, 1605 cm$^{-1}$; MS (m/z) 253 (M+).

Elemental analysis for $C_{14}H_{11}N_3O_2$ Calc'd: C, 66.40; H, 4.38; N, 16.59; Found: C, 66.06; H, 4.35; N, 16.32.

EXAMPLE 21

4-8
3,4-Dioxo-2-(1,2,2-trimethyl-propylamino)-cyclobut-1-enylamino]-benzonitrile Step 1

Preparation of
4-(3,4-Dioxo-2-ethoxy-cyclobut-1-enylamino)-benzonitrile

4-Aminobenzonitrile (3.47 g, 29.4 mmol) was added to a solution of 3,4-diethoxy-3-cyclobutene-1,2-dione (5.00 g, 29.4 mmol) in absolute ethanol (100 mL). The mixture was heated at reflux overnight. The mixture was cooled, and the resulting yellow precipitate was collected by vacuum filtration. Yield: 2.60 g (37%): mp 218°–222° C.

Step 2

Preparation of
4-[3,4-Dioxo-2-(1,2,2-trimethyl-propylamino)-cyclobut-1-enylamino-]-benzonitrile To the above squarate (1.00 g, 4.13 mmol) in acetonitrile (250 mL) was added 2-amino-3,3-dimethylbutane (0.600 mL, 4.48 mmol). A precipitate forms while stirring overnight. The crude reaction mixture is vacuum filtered. The solid is triturated with diethylether to afford 0.620 g (50%) of product as a yellow solid: mp 241°–243° C.; $^1$H NMR (DMSO-$d_6$): δ9.89 (s, 1H), 7.78 (d, 2H), 7.72 (d, 1H), 7.60 (d, 2H), 3.95–4.00 (m, 1H), 1.18 (d, 3H), 0.91 (s, 9H). IR (KBr): 3200, 1790, 1660, 1600 cm$^{-1}$; MS (m/z) 297 (M+).

Elemental analysis for $C_{17}H_{19}N_3O_2$ Calc'd: C, 68.67; H, 6.44; N, 14.13; Found: C, 68.63; H, 6.15; N, 14.30.

EXAMPLE 22

(Exo)-4-[2-(bicyclo[2,2,1]hept-2-ylamino)-3,4-dioxo-cyclobut-1-enylamino]-benzonitrile To the product of Example 21, Step 1 (0.368 g, 1.52 mmol) in acetonitrile (30 mL) was added (±)exo-2-aminonorbornane (0.180 mL, 1.52 mmol). A precipitate forms while stirring overnight. The crude reaction mixture was vacuum filtered and triturated with diethylether to afford 0.370 g (79%) of a yellow solid: mp 288°–290° C.; $^1$H NMR (DMSO-$d_6$): δ9.79 (s, 1H), 7.78 (d, 2H), 7.76 (m, 1H), 7.58 (d, 2H) 3.90–3.98 (m, 1H), 2.22–2.34 (m, 2H), 1.76–1.86 (m, 1H), 1.08–1.56 (m, 7H). IR (KBr): 2220, 1790, 1650, 1600 cm$^{-1}$; MS (m/z) 307 (M+).

Elemental analysis for $C_{18}H_{17}N_3O_2$ Calc'd: C, 70.34; H, 5.57; N, 13.67; Found: C, 70.17; H, 5.50; N, 13.96.

EXAMPLE 23

4-[3,4-Dioxo-2-(1,2,2-trimethyl-propylamino)-cyclobut-1-enylamino]-benzenesulfonamide To a slurry of sulfanilamide (1.72 g, 10.0 mmol) in ethanol (10 mL) was added 3,4-diethoxy-3-cyclobutene-1,2-dione (2.43 g, 14.3 mmol). The reaction was heated at reflux overnight, cooled, and a yellow precipitate was collected by vacuum filtration. Yield: 2.60 g (98%): mp 210°–212° C.

To the above squarate (0.750 g, 2.84 mmol) in ethanol (10 mL) was added 2-amino-3,3-dimethylbutane (0.380 mL, 2.84 mmol). The mixture was heated to reflux overnight then concentrated. The residue was dissolved in acetone/ethylacetate (1:1) and filtered through a plug of silica gel to afford 0.200 g (20%) of the title compound as a white solid, hemi-hydrate: mp 233°–235° C.; $^1$H NMR (DMSO-$d_6$): δ9.87 (s, 1H), 7.79 (d, 2H), 7.75 (d, 1H), 7.58 (d, 2H), 7.25 (s, 2H), 4.00 (m, 1H), 1.18 (d, 3H), 0.92 (s, 9H). IR (KBr): 1790, 1670, 1600 cm$^{-1}$; MS (m/z) 351 (M+).

Elemental analysis for $C_{16}H_{21}N_3O_4S·\frac{1}{2}H_2O$ Calc'd: C, 53.32; H, 6.15; N, 11.66; Found: C, 52.89; H, 5.81; N, 11.42.

The smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The bladder is removed into warm (37 deg. C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following one further 30 minute period of recovery, an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips

| Compound | no. of animals | $IC_{50}$ | Inhibition of Force (%) at (x) μM |
|---|---|---|---|
| Example 1 | 6 | 1.36 μM | — |
| Example 2 | 2 | 15.85 μM | — |
| Example 3 | 3 | 1.95 μM | — |
| Example 6 | 2 | — | 31% (30 μM) |
| Example 7 | 2 | 2.8 μM | — |
| Example 8 | 4 | 1.84 μM | — |
| Example 9 | 4 | — | 43% (30 μM) |
| Example 10 | 4 | 8.0 μM | — |
| Example 14 | 4 | — | 51% (30 μm) |
| Example 19 | 4 | 6.34 μM | — |

TABLE I-continued

Inhibition of Contractions in Isolated Rat Bladder Strips

| Compound | no. of animals | IC$_{50}$ | Inhibition of Force (%) at (x) μM |
|---|---|---|---|
| Example 21 | 2 | 0.52 μM | — |

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally, or by aspiration to a patient in need thereof.

What is claimed is:

1. A compound of the formula:

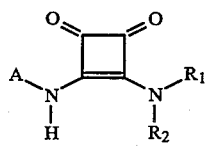
(I)

wherein:
R$_1$ and R$_2$ are, independent from each other, hydrogen, C$_{1-10}$ straight chain alkyl, C$_{1-10}$ branched chain alkyl or C$_{3-10}$ cyclic or bicyclic alkyl;
A is a benzodiazole of the formula:

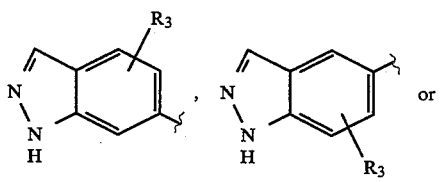

wherein:
R$_3$ is hydrogen, C$_{1-6}$ alkyl, C$_{1-6}$ perfluoroalkyl, C$_{1-6}$ alkoxy, C$_{1-6}$ perfluoroalkoxy, amino, C$_{1-6}$ alkylamino, C$_{2-12}$ dialkylamino, C$_{1-6}$ alkylsulfonamido, alkylcarboxamido containing 2 to 7 carbon atoms, nitro, cyano or carboxyl;
or a pharmaceutically acceptable salt thereof.

2. A compound of claim 1 in which A is an indazole of the following formula:

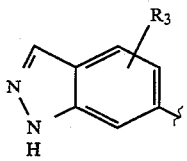

wherein:
R$_3$ is hydrogen, C$_{1-6}$ alkyl, C$_{1-6}$ perfluoroalkyl, C$_{1-6}$ alkoxy, C$_{1-6}$ perfluoroalkoxy, amino, C$_{1-6}$ alkylamino, C$_{2-12}$ dialkylamino, C$_{1-6}$ alkylsulfonamido, alkylcarboxamido containing 2 to 7 carbon atoms, nitro, cyano or carboxyl;
or a pharmaceutically acceptable salt thereof.

3. A compound of claim 1 which is 3-tert-butylamino-4-(1H-indazol-6-ylamino)-cyclobut-3-ene-1,2-dione or a pharmaceutically acceptable salt thereof.

4. A method for reducing the adverse effects of smooth muscle contractions which comprises administering, orally or parenterally, to a patient in need thereof, a compound of the formula:

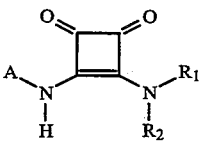
(I)

wherein:
R$_1$ and R$_2$ are, independent from each other, hydrogen, C$_{1-10}$ straight chain alkyl, C$_{1-10}$ branched alkyl, or C$_{3-10}$ cyclic or bicyclic alkyl; and,
A is a benzodiazole of the formula:

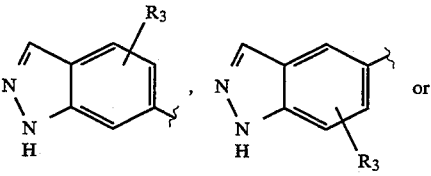

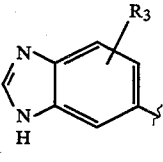

wherein:
R$_3$ is hydrogen, C$_{1-6}$ alkyl, C$_{1-6}$ perfluoroalkyl, C$_{1-6}$ alkoxy, C$_{1-6}$ perfluoroalkoxy, amino, C$_{1-6}$ alkylamino, C$_{2-12}$ dialkylamino, C$_{1-6}$ alkylsulfonamido, alkylcarboxamido containing 2 to 7 carbon atoms, nitro, cyano or carboxyl;
or a pharmaceutically acceptable salt thereof.

5. The method of claim 4 in which the smooth muscle adversely contracting causes urinary incontinence.

6. The method of claim 4 in which the smooth muscle adversely contracting causes irritable bowel syndrome.

* * * * *